(12) United States Patent
Lantz

(10) Patent No.: US 9,468,400 B2
(45) Date of Patent: Oct. 18, 2016

(54) AUDIOLOGIC TEST APPARATUS WITH DUAL PROBE SYSTEM

(71) Applicant: GN Otometrics A/S, Taastrup (DK)

(72) Inventor: Johannes Lantz, Malmo (SE)

(73) Assignee: GN OTOMETRICS A/S, Taastrup (DK)

( * ) Notice: Subject to any disclaimer, the term of this patent is extended or adjusted under 35 U.S.C. 154(b) by 238 days.

(21) Appl. No.: 14/292,337

(22) Filed: May 30, 2014

(65) Prior Publication Data

US 2015/0342504 A1 Dec. 3, 2015

(30) Foreign Application Priority Data

May 28, 2014 (DK) .................................. 2014 70305
May 28, 2014 (EP) ..................................... 14170297

(51) Int. Cl.
*A61B 5/12* (2006.01)
*A61B 5/00* (2006.01)

(52) U.S. Cl.
CPC ................ *A61B 5/121* (2013.01); *A61B 5/125* (2013.01); *A61B 5/6817* (2013.01); *A61B 5/6844* (2013.01); *A61B 2560/0443* (2013.01)

(58) Field of Classification Search
CPC ...... A61B 5/12; H04R 25/50; H04R 25/502; H04R 25/505; H04R 25/507; H04R 25/70
USPC .......................................................... 73/585
See application file for complete search history.

(56) References Cited

U.S. PATENT DOCUMENTS

| 4,014,320 | A | 3/1977 | Richards |
| 4,029,083 | A | 6/1977 | Baylor |
| 4,079,198 | A | 3/1978 | Bennett |
| 2004/0184618 | A1 | 9/2004 | Bengtsson |
| 2006/0074341 | A1 | 4/2006 | Causevic et al. |
| 2007/0112279 | A1 | 5/2007 | Iseberg et al. |
| 2009/0321177 | A1 | 12/2009 | Mcmahon et al. |
| 2011/0224493 | A1* | 9/2011 | Oyadiran ........... A61B 1/00016 600/200 |
| 2012/0302859 | A1 | 11/2012 | Keefe |

OTHER PUBLICATIONS

Second Technical Examination dated Jun. 4, 2015 for corresponding Danish Patent Application No. PA 2014 70305, 3 pages.

(Continued)

*Primary Examiner* — Laura Martin
*Assistant Examiner* — Rose M Miller
(74) *Attorney, Agent, or Firm* — Vista IP Law Group, LLP

(57) ABSTRACT

An audiologic test apparatus includes: a processing unit configured to conduct a first and second audiologic tests; a first probe connector for connecting a first probe for the first audiologic test; a second probe connector for connecting a second probe for the second audiologic test; and a pump module connected to a first fluid port of the first probe connector with a first fluid channel and to a second fluid port of the second probe connector with a second fluid channel, wherein the pump module in a first operating mode is in fluid communication with the first fluid port, and in a second operating mode is in fluid communication with the second fluid port, the pump module configured to modify pressure in the first fluid channel when in the first operating mode, and to modify pressure in the second fluid channel when in the second operating mode.

16 Claims, 6 Drawing Sheets

(56) References Cited

OTHER PUBLICATIONS

Third Technical Examination—Intention to Grant dated Sep. 14, 2015 for corresponding Danish Patent Application No. PA 2014 70305, 2 pages.

Extended European Search Report dated Oct. 9, 2014, for related EP 14170297.7, 9 pages.
First Technical Examination Report and Search Report dated Dec. 11, 2014, for related Danish Patent Application No. PA 2014 70305, 8 pages.

* cited by examiner

AUDIOLOGIC TEST APPARATUS WITH DUAL PROBE SYSTEM

RELATED APPLICATION DATA

This application claims priority to and the benefit of Danish Patent Application No. PA 2014 70305, filed May 28, 2014, pending, and European Patent Application No. 14170297.7, filed on May 28, 2014, pending. The entire disclosures of both of the above applications are expressly incorporated by reference herein.

FIELD

The present disclosure relates to an audiologic test apparatus. In particular, the present disclosure relates to an audiologic test apparatus used to perform different audiologic tests, such as acoustic reflex, acoustic reflex threshold, tympanometric and/or otoacoustic emission tests.

BACKGROUND

In order to perform an audiologic test, such as an acoustic reflex test, acoustic reflex threshold test, tympanometric test and/or otoacoustic emission tests, a probe needs to be positioned in the ear canal. However, specific audiologic tests may require different probes, or have different requirements to the probe. For example, a screening type acoustic reflex test may be performed with a hand-held probe, whereas a diagnostic type acoustic reflex test (also known as an acoustic reflex threshold test) may require a probe fitted and retained in the ear of a user.

Furthermore, it may be desirable that the probe is as simple as possible in order to perform the test as convenient and easy as possible. Thus, a probe fulfilling the technical requirements of all audiologic tests may be undesirable to use in some audiologic tests, e.g. due to timely and/or uneasy fitting. For example, a probe being fitted and retained in the ear of the user may be used for both screening type and diagnostic type acoustic reflex tests, but due to easiness of using a hand-held probe and the fact that most acoustic reflex tests are screening type acoustic reflex tests it is desirable to have a hand-held probe.

SUMMARY

Previously, the problem may have been addressed, either by having a plurality of apparatuses, e.g. one for each audiologic test, or employing a configurable probe, which in one configuration was suitable for one audiologic test and in another configuration suitable for another audiologic test. However, having a plurality of apparatuses is both expensive and takes up excess space, and a configurable probe is inherently in need of configuration, thus being inappropriately time consuming.

Hence, despite the known solutions there is a need for an audiologic test apparatus that provides for easy performance of different audiologic tests, wherein the audiologic tests have different requirements to the probe, e.g. screening type and diagnostic type acoustic reflex tests.

Accordingly, an audiologic test apparatus is provided. The audiologic test apparatus comprises: a processing unit, a first probe connector, a second probe connector, and a pump module. The processing unit is configured to conduct a set of audiologic tests including a first audiologic test and a second audiologic test. The first probe connector is for connecting a first probe for the first audiologic test. The first probe connector is connected to the processing unit and comprises a first fluid port. The second probe connector is for connecting a second probe for the second audiologic test. The second probe connector is connected to the processing unit and comprises a second fluid port. The pump module is connected to the first fluid port with a first fluid channel and the second fluid port with a second fluid channel. The pump module in a first operating mode is configured to be in fluid communication with the first fluid port, and in a second operating mode is configured to be in fluid communication with the second fluid port. The pump module is configured to modify pressure in the first fluid channel when conducting the first audiologic test in the first operating mode, and the pump module is configured to modify pressure in the second fluid channel when conducting the second audiologic test in the second operating mode.

Also disclosed is an audiologic test system comprising: an audiologic test apparatus such as the audiologic test apparatus, a first probe, and a second probe. The audiologic test apparatus comprises a pump module and a processing unit configured to conduct a set of audiologic tests including a first audiologic test and a second audiologic test. The first probe is configured for the first audiologic test. The first probe is connected to the processing unit and comprises a first fluid port connected to the pump module. The second probe is configured for the second audiologic test. The second probe is connected to the processing unit and comprises a second fluid port connected to the pump module.

The pump module is connected to the first fluid port with a first fluid channel and the second fluid port with a second fluid channel. The pump module in a first operating mode is configured to be in fluid communication with the first fluid port, and in a second operating mode is configured to be in fluid communication with the second fluid port. The pump module is configured to modify pressure in the first fluid channel when conducting the first audiologic test in the first operating mode, and to modify pressure in the second fluid channel when conducting the second audiologic test in the second operating mode.

Also disclosed is a method for operating an audiologic test system such as the audiologic test system, and/or an audiologic test apparatus such as the audiologic test apparatus, configured to conduct a set of audiologic tests including a first audiologic test and a second audiologic test. The audiologic test system or the audiologic test apparatus comprises a first probe configured for the first audiologic test or a first probe connector for connecting the first probe. The first probe comprises a first fluid port. The audiologic test system or the audiologic test apparatus comprises a second probe configured for the second audiologic test or a first probe connector for connecting the first probe, the second probe comprising a second fluid port. The audiologic test system or the audiologic test apparatus comprises a pump module connected to the first fluid port and the second fluid port.

The method comprising: selecting an audiologic test of the first audiologic test and the second audiologic test; configuring the pump module to be in fluid communication with the first fluid port if the selected audiologic test is the first audiologic test; configuring the pump module to be in fluid communication with the second fluid port if the selected audiologic test is the second audiologic test.

It is an advantage that easy switching be provided between a plurality of audiologic tests, and that a single apparatus may be provided for conducting a plurality of audiologic tests. It is an even further advantage of the present disclosure, that time consuming and cumbersome configuration of test probes is avoided or at least reduced.

An audiologic test apparatus includes: a processing unit configured to conduct a set of audiologic tests including a first audiologic test and a second audiologic test; a first probe connector for connecting a first probe for the first audiologic test, wherein the first probe connector is connected to the processing unit and comprises a first fluid port; a second probe connector for connecting a second probe for the second audiologic test, wherein the second probe connector is connected to the processing unit and comprises a second fluid port; and a pump module connected to the first fluid port with a first fluid channel and to the second fluid port with a second fluid channel, wherein the pump module in a first operating mode is configured to be in fluid communication with the first fluid port, and in a second operating mode is configured to be in fluid communication with the second fluid port, the pump module being configured to modify pressure in the first fluid channel when conducting the first audiologic test in the first operating mode, and to modify pressure in the second fluid channel when conducting the second audiologic test in the second operating mode.

Optionally, the first audiologic test comprises a first set of subtests and the second audiologic test comprises the first set of subtests and a second set of subtests.

Optionally, the first probe connector comprises one or more first terminals for electrically connecting the audiologic test apparatus and the first probe. Optionally, the processing unit is configured to select an audiologic test to be performed based on one or more control signals, wherein the selected audiologic test comprises the first audiologic test, the second audiologic test, or another audiologic test.

Optionally, the audiologic test apparatus further includes a user interface, wherein the user interface comprises a selector with at least a first selector position and a second selector position, wherein the selector is connected to the processing unit, and wherein the one or more control signals comprises a selector signal indicative of at least the first selector position or the second selector position.

Optionally, the one or more control signals comprise a first electrical probe signal from the first probe.

Optionally, the pump module comprises a first pump and a second pump, wherein the first pump is connected to the first fluid port and the second pump is connected to the second fluid port.

Optionally, the pump module comprises a first pump and a connector module, wherein the connector module is configured to connect the first pump and the first fluid port in the first operating mode, and the connector module is configured to connect the first pump and the second fluid port in the second operating mode.

Optionally, the audiologic test apparatus further includes a first tone generator connected to the first probe connector, the first tone generator configured to generate a first primary test signal for the first probe when the first probe is connected to the first probe connector.

Optionally, the first tone generator is configured to generate a first secondary test signal for the first probe when the first probe is connected to the first probe connector.

Optionally, the processing unit is configured to detect a connection of the first probe to the first probe connector.

Optionally, the processing unit is configured to configure the first audiologic test based on an identification signal indicative of the first probe.

Optionally, the processing unit is configured to initiate the first operating mode in response to the first probe being selected; and initiate the second operating mode in response to the second probe being selected.

A method for operating an audiologic test system configured to conduct a set of audiologic tests including a first audiologic test and a second audiologic test, wherein the audiologic test system comprises a first probe configured for the first audiologic test, the first probe comprising a first fluid port, and wherein the audiologic test system further comprises a second probe configured for the second audiologic test, the second probe comprising a second fluid port, the audiologic test system comprising a pump module connected to the first fluid port and the second fluid port, the method includes: selecting an audiologic test from the first audiologic test and the second audiologic test; configuring the pump module to be in fluid communication with the first fluid port if the selected audiologic test is the first audiologic test; and configuring the pump module to be in fluid communication with the second fluid port if the selected audiologic test is the second audiologic test;

Optionally, the method further includes: connecting the first probe to a first probe connector of the audiologic test system; and connecting the second probe to a second probe connector of the audiologic test system.

An audiologic test system includes: an audiologic test apparatus comprising a pump module and a processing unit configured to conduct a set of audiologic tests including a first audiologic test and a second audiologic test; a first probe configured for the first audiologic test, wherein the first probe is connected to the processing unit and comprises a first fluid port connected to the pump module; and a second probe configured for the second audiologic test, wherein the second probe is connected to the processing unit and comprises a second fluid port connected to the pump module; wherein the pump module is connected to the first fluid port with a first fluid channel and to the second fluid port with a second fluid channel, wherein the pump module in a first operating mode is configured to be in fluid communication with the first fluid port, and in a second operating mode is configured to be in fluid communication with the second fluid port, the pump module being configured to modify pressure in the first fluid channel when conducting the first audiologic test in the first operating mode, and to modify pressure in the second fluid channel when conducting the second audiologic test in the second operating mode.

Optionally, the first probe is configured to generate a first control signal indicative of the first audiologic test.

Other and further aspects and features will be evident from reading the following detailed description.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
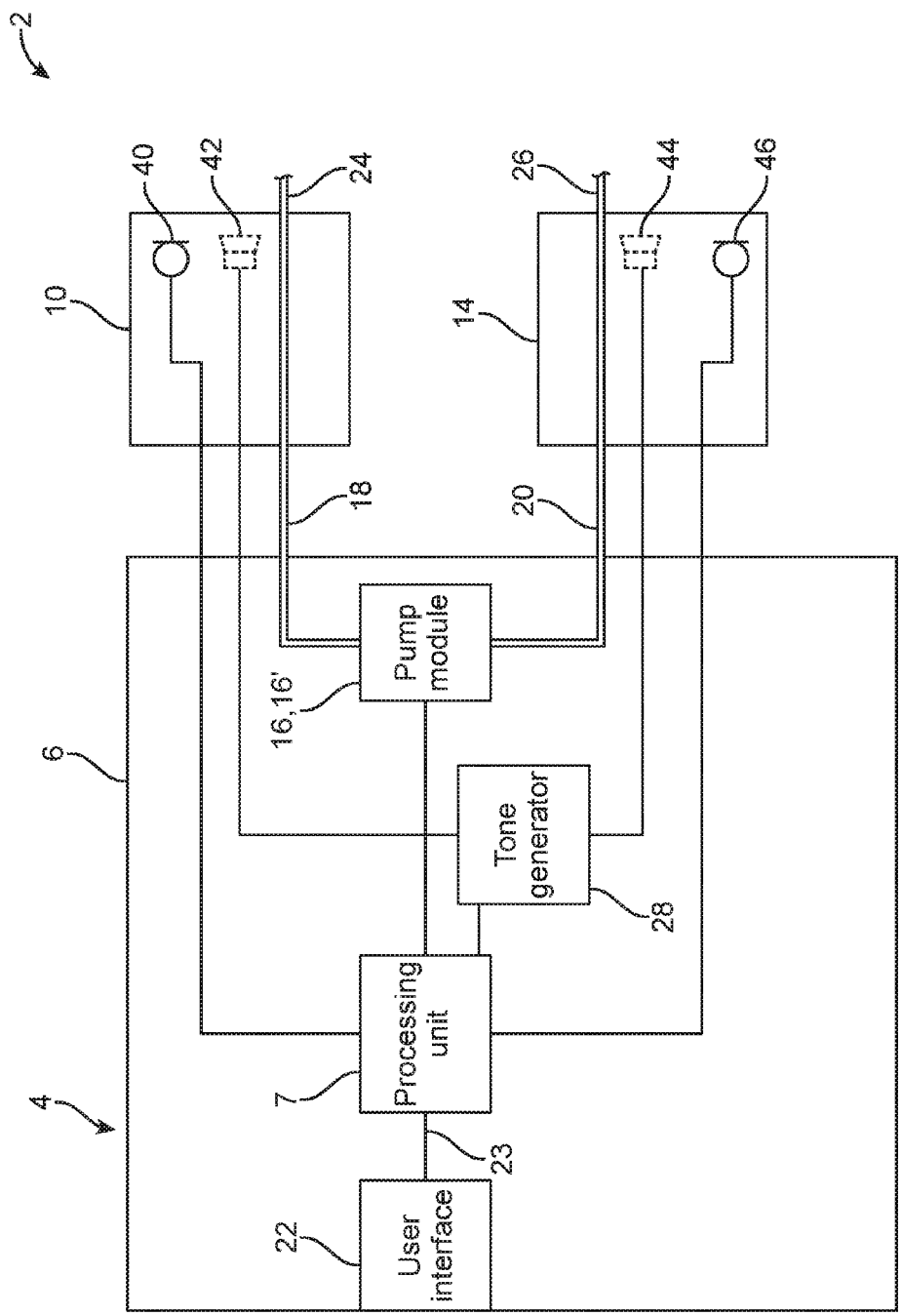
FIG. 1 schematically illustrates an exemplary audiologic test system and an exemplary test apparatus, FIG. 2 schematically illustrates an exemplary audiologic test system and an exemplary test apparatus, FIG. 3 schematically illustrates an exemplary first probe for an audiologic test system, FIG. 4 schematically illustrates an exemplary second probe for an audiologic test system, FIG. 5 schematically illustrates an exemplary pump module, FIG. 6 schematically illustrates an exemplary pump module.

Various features are described hereinafter with reference to the figures. It should be noted that the figures may or may not be drawn to scale and that the elements of similar structures or functions are represented by like reference numerals throughout the figures. It should be noted that the figures are only intended to facilitate the description of the features. They are not intended as an exhaustive description of the claimed invention or as a limitation on the scope of the claimed invention. In addition, an illustrated feature needs not have all the aspects or advantages shown. An aspect or an advantage described in conjunction with a particular feature is not necessarily limited to that feature and can be practiced in any other features even if not so illustrated or if not so explicitly described.

The audiologic test apparatus may comprise a housing. The housing may enclose the pump module and/or the processing unit. The housing may comprise one or more probe connectors, such as the first probe connector and/or the second probe connector. The one or more probe connectors may be positioned in a wall of the housing, such as to provide a connection between a component inside the housing, such as the pump module, and another component outside the housing, such as a probe.

The method of operating the audiologic test apparatus and/or system may further comprise connecting a probe to a probe connector. For example, the method of operating the audiologic test apparatus and/or system may comprise connecting the first probe to a first probe connector and/or connecting the second probe to a second probe connector.

The one or more probe connectors may provide a fixed connection of a probe, such as the first probe and/or the second probe. The one or more probe connectors may be configured for detachably connecting a probe, such as the first probe and/or the second probe. In an exemplary audiologic test apparatus and/or system, one probe, e.g. the first probe, may be fixedly connected with the first probe connector, and another probe, e.g. the second probe may be detachably connected with the second probe connector. In another exemplary audiologic test apparatus and/or system, one probe, e.g. the second probe, may be fixedly connected with the second probe connector, and another probe, e.g. the first probe may be detachably connected with the first probe connector.

The processing unit may comprise a memory module. The processing unit may comprise a central processing unit. The processing unit may comprise one or more input ports. The processing unit may comprise one or more output ports.

The processing unit may be configured to conduct a set of audiologic tests. The set of audiologic tests may comprise a first audiologic test, a second audiologic test, a third audiologic test, a fourth audiologic test and/or a fifth audiologic test. The first audiologic test may comprise a screening type acoustic reflex test. The second audiologic test may comprise a diagnostic type acoustic reflex test.

An audiologic test may comprise a set of subtests. The first audiologic test may comprise a first set of subtests, e.g. a tympanogram. The second audiologic test may comprise the first set of subtests and a second set of subtests, e.g. a diagnostic type reflex test. For example, the first audiologic test may comprise a tympanogram, and the second audiologic test may comprise a tympanogram and a diagnostic type reflex test.

A probe connector may comprise one or more terminals for electrically connecting the audiologic test apparatus and a probe. For example, the first probe connector may comprise one or more first terminals for electrically connecting the audiologic test apparatus and the first probe and/or the second probe connector may comprise one or more second terminals for electrically connecting the audiologic test apparatus and the second probe.

The probe, such as the first probe and/or the second probe may comprise a speaker and/or a microphone. The terminals, such as the first terminals and/or the second terminals, may comprise one or more microphone terminals for receiving an electrical signal from the microphone. Alternatively or additionally, the terminals, such as the first terminals and/or the second terminals, may comprise one or more speaker terminals for providing an electrical signal to the speaker. The first probe may be a screening probe, i.e. configured for a screening type audiologic test, such as a screening type acoustic reflex test. The second probe may be a diagnostic probe, i.e. configured for a diagnostic type audiologic test, such as a diagnostic type acoustic reflex test.

The processing unit may be configured to select an audiologic test to be performed based on one or more control signals. The control signal may be indicative of the first audiologic test and/or the second audiologic test. The control signal may be indicative of a probe, such as the first probe or the second probe, in use.

The audiologic test apparatus and/or system may comprise a user interface. The user interface may comprise a display, such as an OLED (organic light emitting diode), LED (light emitting diode) or LCD (liquid crystal display). The user interface may comprise a selector with at least a first selector position and a second selector position. The selector may be connected to the processing unit. The one or more control signals may comprise a selector signal indicative of at least the first selector position and/or the second selector position. The selector may be a touch display.

The audiologic test apparatus and/or system may be configured to detect if a probe, such as the first probe and/or the second probe is inserted into an ear canal. The probe, such as the first probe and/or the second probe, may transmit a test tone, e.g. in the range from 20-1,500 Hz, such as 226 Hz and/or 1,000 Hz. A microphone may detect a reflection of the test tone. The detected reflection may be used as an indicator that the probe is inserted into an ear canal.

Hence, the one or more control signals may comprise an electrical probe signal from a probe, e.g. a microphone signal. For example, the one or more control signals may comprise a first electrical probe signal from the first probe. Alternatively or additionally, the one or more control signals may comprises a second electrical probe signal from the second probe.

The audiologic test apparatus and/or system may be configured to: detect whether the first or the second probe has been selected; and to initiate the first operating mode if the first probe has been selected; and to initiate the second operating mode if the second probe has been selected. Selection of the first or second probe may be detected as described above, such as utilizing a user interface, a selector and/or detection of insertion of the first or the second probe in an ear canal. Detection of insertion may be based on an audio test signal and/or light intensity detection.

The pump module may comprise a first pump and/or a second pump. The first pump may be connected to the first fluid port. The second pump may be connected to the second fluid port.

The pump module may comprise a connector module. The connector module may be configured to connect the first pump and the first fluid port in the first operating mode. The connector module may be configured to connect the first pump and the second fluid port in the second operating mode.

The audiologic test apparatus may comprise one or more tone generators including a first tone generator and/or a second tone generator. The one or more tone generators may be connected to the one or more of the probe connectors, such as the first probe connector and/or the second probe connector, or connected to one or more probes, such as the first probe and/or the second probe. The one or more tone generators may be configured to generate a primary test signal, and/or a secondary test signal, for one or more probes connected to the one or more probe connectors. For example, The first tone generator may be connected to the first probe connector, and the first tone generator may be configured to generate a first primary test signal for the first probe connected to the first probe connector. Alternatively or additionally, the first tone generator may be connected to the first probe connector and the second probe connector, and the first tone generator may be configured to generate a first primary test signal for the first probe connected to the first probe connector and the second probe connected to the second probe connector. Alternatively or additionally, the audiologic test apparatus may comprise a second tone generator connected to the second probe connector, and the second tone generator may be configured to generate a second primary test signal for the second probe connected to the second probe connector.

The first primary test signal and/or the second primary test signal may be a speaker signal for emitting an acoustic signal from a speaker. The first primary test signal and/or the second primary test signal may comprise a primary frequency component at a primary frequency, e.g. around 226 Hz or around 1000 Hz.

The first tone generator may be configured to generate a first secondary test signal for the first probe connected to the first probe connector and/or for the second probe connected to the second probe connector. The second tone generator may be configured to generate a second secondary test signal for the second probe connected to the second probe connector.

The first secondary test signal and/or the second secondary test signal may be a speaker signal for emitting an acoustic signal from a speaker. The first secondary test signal and/or the second secondary test signal may comprise a secondary frequency component at a secondary frequency. The secondary frequency and the primary frequency may be the same frequency, e.g. around 226 Hz or around 1000 Hz.

The processing unit may be configured to detect connection of a probe, e.g. the first probe and/or the second probe, to a probe connector, e.g. the first probe connector and/or the second probe connector.

The processing unit may be configured to configure an audiologic test based on an identification signal indicative of a probe, a probe ID or other information enabling the audiologic test apparatus to identify the test to be performed with the probe connected to the respective probe connector. For example, the processing unit may be configured to configure the first audiologic test based on an identification signal indicative of the first probe or a probe ID indicative of the probe connected to the first probe connector. Alternatively or in combination, the processing unit may be configured to configure the second audiologic test based on an identification signal indicative of the second probe or a probe ID indicative of the probe connected to the second probe connector.

In an exemplary audiologic test apparatus and/or system, the first probe may be suitable for the first audiologic test comprising a screening type acoustic reflex test.

A connected probe, e.g. a first probe connected to the first probe connector and/or a second probe connected to the second probe connector, may indicate probe ID or other information indicative of test type or probe type to the processing unit by sending an identification signal to the audiologic test apparatus. In an exemplary audiologic test apparatus or system, the audiologic test apparatus may be configured to obtain a probe ID, e.g. from the probe when the probe is connected to a probe connector, the user interface or a memory. The probe ID may be indicative of probe type, test type and/or probe model. The audiologic test apparatus may be configured to apply an audiologic test based on the obtained probe ID. Thus, the processing unit may configure the first audiologic test to comprise a screening type acoustic reflex test.

A probe, such as the first probe and/or the second probe, may be configured to generate one or more control signals including the control signal. For example, the first probe may be configured to generate a first control signal indicative of the first audiologic test. Alternatively or additionally, the second probe may be configured to generate a second control signal indicative of the second audiologic test.

FIG. 1 schematically illustrates an exemplary audiologic test system 2. The audiologic test system 2 comprises an exemplary audiologic test apparatus 4, a first probe 10 and a second probe 14. The audiologic test apparatus 4 comprises a housing 6, a processing unit 7, a pump module 16, 16', an optional user interface 22, and an optional tone generator 28.

The processing unit 7 (audiologic test apparatus) is configured to conduct a set of audiologic tests including a first audiologic test and a second audiologic test. For example, the first audiologic test may comprise a screening type acoustic reflex test, and the second audiologic test may comprise a diagnostic type acoustic reflex test.

The first probe 10 is configured for the first audiologic test. For example, the first probe 10 may be a hand-held probe suitable for a screening type acoustic reflex test. The first probe 10 is connected to the processing unit 7, and the first probe 10 comprises a first fluid port 24.

The second probe 14 is configured for the second audiologic test. For example, the second probe 14 may be an earplug type probe suitable for a diagnostic type acoustic reflex test. The second probe 14 is connected to the processing unit 7, and the second probe 14 comprises a second fluid port 26.

The tone generator 28 is connected to the first probe 10 and the second probe 14. The tone generator 28 may be configured to generate a test signal for the first probe 10 and/or the second probe 14.

The first probe 10 comprises a first microphone 40 and a first speaker 42. The first microphone 40 is connected to the processing unit 7 of the audiologic test apparatus 4. The first speaker 42 is connected to the tone generator 28. The first speaker 42 is configured to receive an electrical signal from the tone generator 28 and convert it to a first acoustic output signal transmitted into the ear canal. The first microphone 40 is configured to receive a first acoustic input signal from within the ear canal, e.g. a reflection or partly reflection of the first acoustic output signal, and convert the received first acoustic input signal to an electrical signal transmitted to the processing unit 7.

The second probe 14 comprises a second microphone 44 and a second speaker 46. The second microphone 44 is connected to the processing unit 7 of the audiologic test apparatus 4. The second speaker 46 is connected to the tone generator 28. The second speaker 46 is configured to receive an electrical signal from the tone generator 28 and convert it to a second acoustic output signal transmitted into the ear canal. The second microphone 44 is configured to receive a second acoustic input signal from within the ear canal, e.g. a reflection or partly reflection of the second acoustic output signal, and convert the received second acoustic input signal to an electrical signal transmitted to the processing unit 7.

Figure 2:
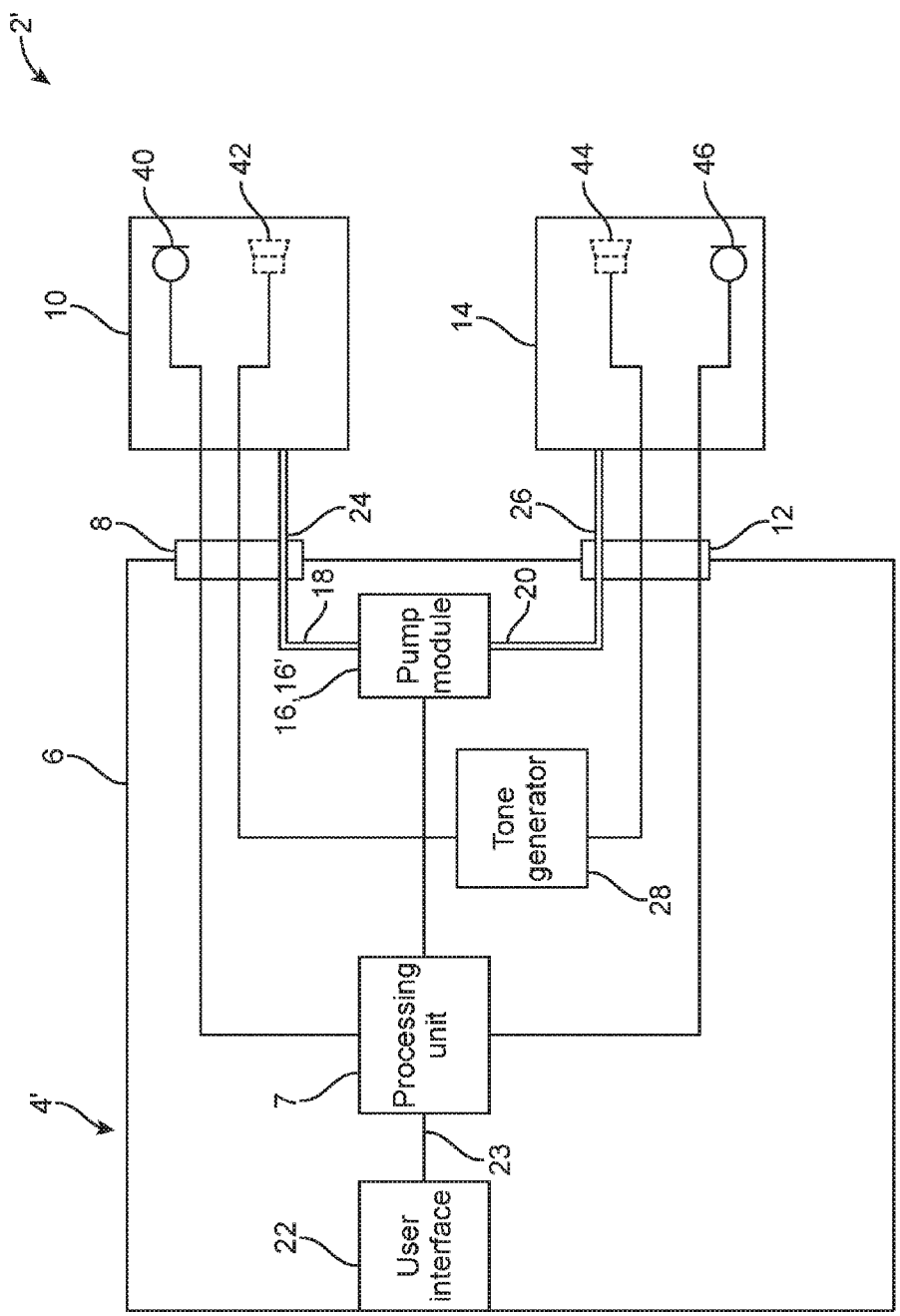

FIG. 2 schematically illustrates an exemplary audiologic test system 2'. The audiologic test system 2' comprises an exemplary audiologic test apparatus 4', a first probe 10, and a second probe 14. The audiologic test apparatus 4' comprises a housing 6, a processing unit 7, a first probe connector 8, a second probe connector 12, a pump module 16, 16', an optional user interface 22 and an optional tone generator 28.

The processing unit 7 is, as explained in relation to FIG. 1, configured to conduct a set of audiologic tests including the first audiologic test and the second audiologic test.

The first probe connector 8 is configured for connecting the first probe 10 to the audiologic test apparatus 4'. The first probe 10 is configured for the first audiologic test. For example, the first probe 10 may be a hand-held probe suitable for a screening type acoustic reflex test. The first probe connector 8 is connected to the processing unit 7, and the first probe connector 8 comprises the first fluid port 24. If the first probe 10 is connected to the first probe connector 8, the first fluid port 24 and the first probe 10 is in fluid communication as illustrated. In an exemplary audiologic test apparatus 4', the first probe 10 is fixedly attached to the first probe connector 8. In another exemplary audiologic test apparatus 4', the first probe 10 is detachably attachable to the first probe connector 8.

The second probe connector 12 is configured for connecting the second probe 14 to the audiologic test apparatus 4. The second probe 14 is configured for the second audiologic test. For example, the second probe 14 may be an earplug type probe suitable for a diagnostic type acoustic reflex test. The second probe connector 12 is connected to the processing unit 7, and the second probe connector 12 comprises the second fluid port 26. If the second probe 14 is connected to the second probe connector 10, the second fluid port 26 and the second probe 14 is in fluid communication as illustrated. In an exemplary audiologic test apparatus 4', the second probe 14 is fixedly attached to the second probe connector 12. In another exemplary audiologic test apparatus 4', the second probe 14 is detachably attachable to the second probe connector 12.

In an exemplary audiologic test apparatus 4' the first probe is fixedly attached to the first probe connector 8 and the second probe 14 is detachably attachable to the second probe connector 12. In an alternative exemplary audiologic test apparatus 4' the first probe is detachably attached to the first probe connector 8 and the second probe 14 is fixedly attachable to the second probe connector 12.

The tone generator 28 is connected to the first probe 10 through the first probe connector 8 and the tone generator 28 is connected to the second probe 14 through the second probe connector 12. The tone generator 28 may be configured to generate a test signal for the first probe 10 and/or the second probe 14.

In relation to the examples of either or both of FIG. 1 and FIG. 2, the pump module 16, 16' is connected to the first fluid port 24 with a first fluid channel 18, and the pump module 16, 16' is connected to the second fluid port 26 with a second fluid channel 20. The pump module 16, 16' may be configured to operate in a plurality of operating modes. In a first operating mode, the pump module 16, 16' is configured to be in fluid communication with the first fluid port 24 via the first fluid channel 18. In a second operating mode, the pump module 16, 16' is configured to be in fluid communication with the second fluid port 26 via the second fluid channel 20. The pump module 16, 16' is configured to modify pressure in the first fluid channel 18 when conducting the first audiologic test in a first operating mode. The pump module 16, 16' is further configured to modify pressure in the second fluid channel 20 when conducting the second audiologic test in a second operating mode.

In an exemplary audiologic test apparatus 4, 4', modifying pressure in the first fluid channel 18 comprise that the second fluid channel 20 is closed, such that the pump module 16, 16' in the first operating mode is not in fluid communication with the second fluid port 26. And vice versa, in modifying pressure in the second fluid channel 20 comprise that the first fluid channel 18 is closed, such that the pump module 16, 16' in the second operating mode is not in fluid communication with the first fluid port 24. The opening and/or closing of the fluid channels 18, 20 are in an exemplary apparatus 4, 4' performed within the pump module 16, 16'. Alternatively, the opening and/or closing of the first and second fluid channels 18, 20 are performed externally to the pump module, e.g. by the first and second probe connectors 8, 12, respectively or by the first and second probes 10, 14, respectively.

The user interface 22 is connected to the processing unit 7. The user interface 22 transmits a control signal 23 to the processing unit 7. The control signal 23 may be transmitted upon interaction from a user, such as an operator of the apparatus 4, 4'. The user interface 22 may comprise a display. The user interface 22 may comprise a selector, such as a touch display, and one or more push buttons. The control signal may comprise a selector signal indicative of a selector position. The processing unit 7 may be configured to select an audiologic test to be performed based on the control signal 23.

Figure 3:
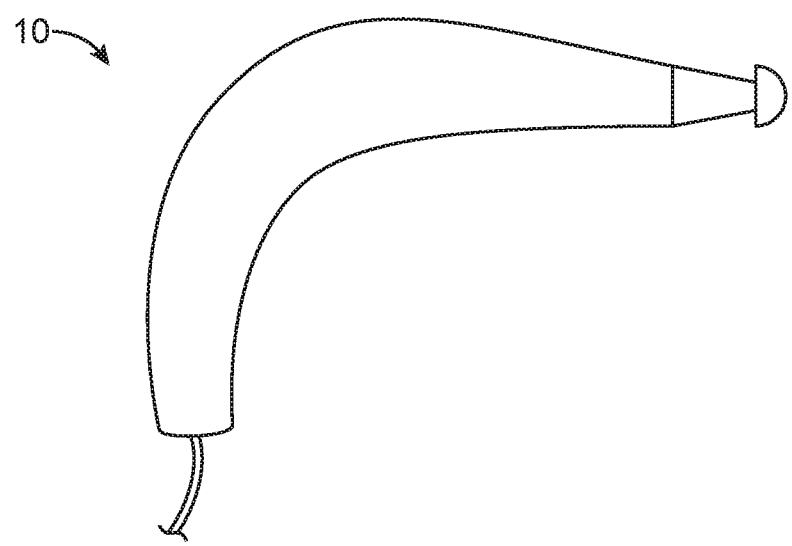

In an embodiment of FIG. 2 and an embodiment of FIG. 3, the fluid channels 18, 20 or fluid ports 24, 26 may be in fluid communication with an ear canal of a user when the respective probes 10, 14 are inserted into an ear of a user.

In an embodiment of FIG. 2 and an embodiment of FIG. 3, the first and second speakers 42 and 44 may be contained in the housing 6 and connected to the processing unit 7. The first and second probes may in these embodiments be connected to the respective first and second speakers via tubes in order to enable sound to be communicated from the respective speakers in the housing to the respective probes 10, 14.

FIG. 3 schematically illustrates an exemplary first probe 10 for an audiologic test system 2, 2'. The first probe 10 is a hand-held probe suitable for a first audiologic test, e.g. a screening type acoustic reflex test. An operator may position the tip of the first probe 10 in the ear canal of a user applying pressure towards the ear canal of the user for creating an air tight seal between the ear canal of the user and the tip of the first probe 10. The operator may continue to apply a pressure towards the ear canal of the user while the first audiologic test is performed by the audiologic test apparatus 4, 4' connected to the first probe 10.

Figure 4:
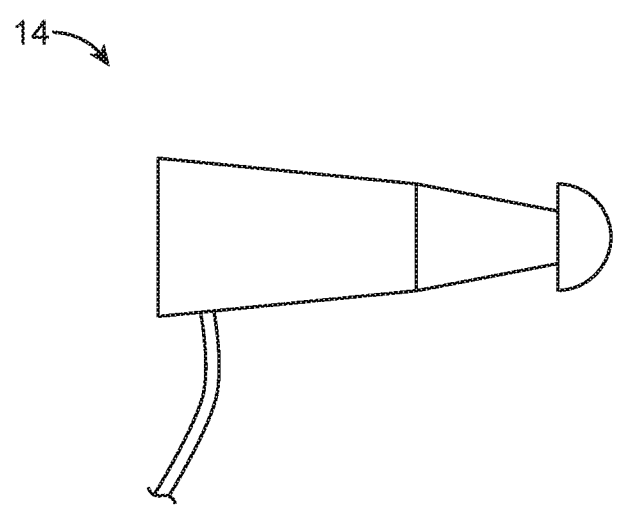

FIG. 4 schematically illustrates an exemplary second probe 14 for an audiologic test system 2, 2'. The second probe 14 is an earplug type probe suitable for a first audiologic test, e.g. a diagnostic type acoustic reflex test. An operator may fit the tip of the second probe 14 into the ear canal of a user by applying pressure towards the ear canal of the user for creating an air tight seal between the ear canal of the user and the tip of the second probe 14. The operator may further verify that the air tight seal is maintained after he let go of his grip of the second probe 14. After installing the second probe 14 in the ear canal of the user, the operator may initiate the performance of the second audiologic test without him touching the second probe 14.

Figure 5:
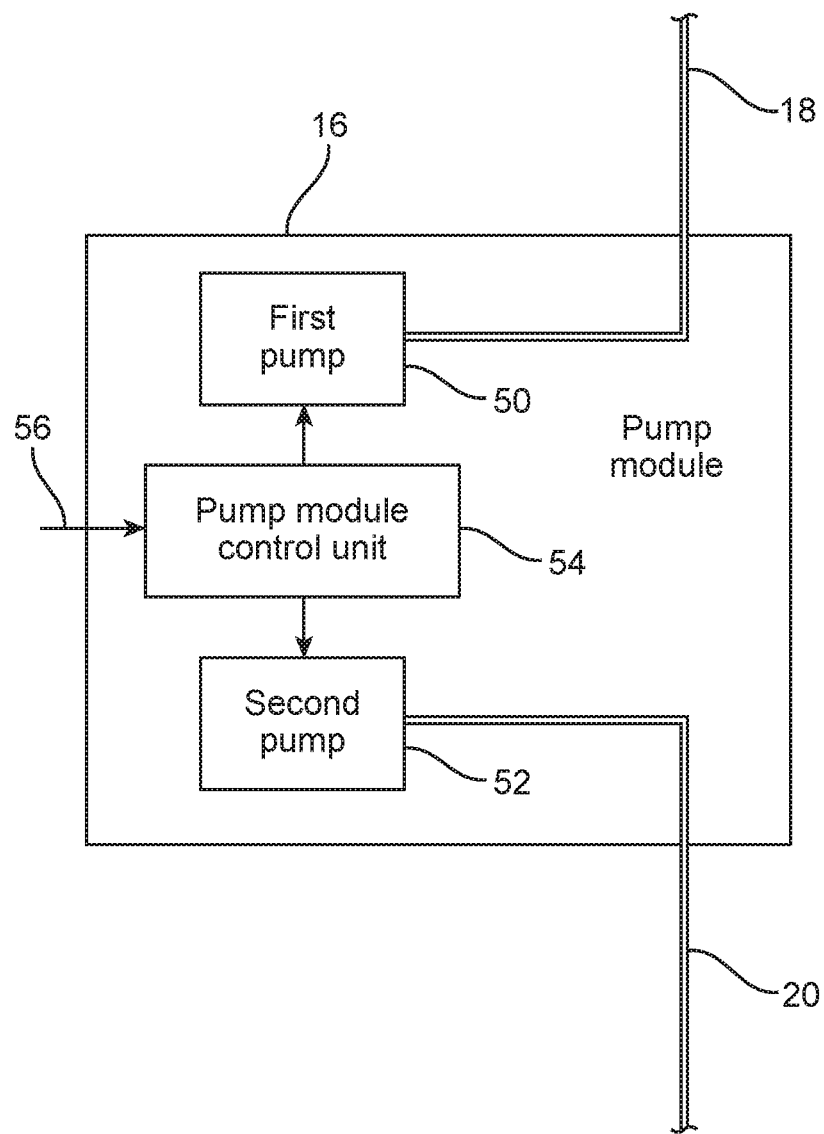

FIG. 5 schematically illustrates an exemplary pump module 16. The pump module 16 comprises a first pump 50, a second pump 52, and a pump module control unit 54. The first pump 50 is connected to the first fluid port 24 (FIGS. 1-2) with the first fluid channel 18. The second pump 52 is connected to the second fluid port 26 (FIGS. 1-2) with the second fluid channel 20. The pump module control unit 54 is connected to the processing unit 7 (FIGS. 1-2), wherefrom the pump module control unit 54 receives a pump module control signal 56. The pump module control unit 54 is connected to the first pump 50 and the second pump 54. The pump module control unit 54 controls the first pump 50 and the second pump 54 based on the pump module control signal 56. For example, in a first operating mode, e.g. when conducting the first audiologic test, the pump module 16 is configured to modify pressure in the first fluid channel 18, by utilizing first pump 50. Vice versa, in a second operating mode, e.g. when conducting the second audiologic test, the pump module 16 is configured to modify pressure in the second fluid channel 20, utilizing the second pump 52. The pump module control unit 54 receives a pump module control signal 56 indicative of which of the fluid channels to modify pressure, the pump module control unit 54 modifies pressure with the first pump 50 if the pressure is to be modified in the first fluid channel 18, or with the second pump 52 if the pressure is to be modified in the second fluid channel 20. The pump module 16 may further comprise one or more pressure sensors (not shown) for measuring the pressure in the first fluid channel 18 and/or in the second fluid channel 20.

Figure 6:
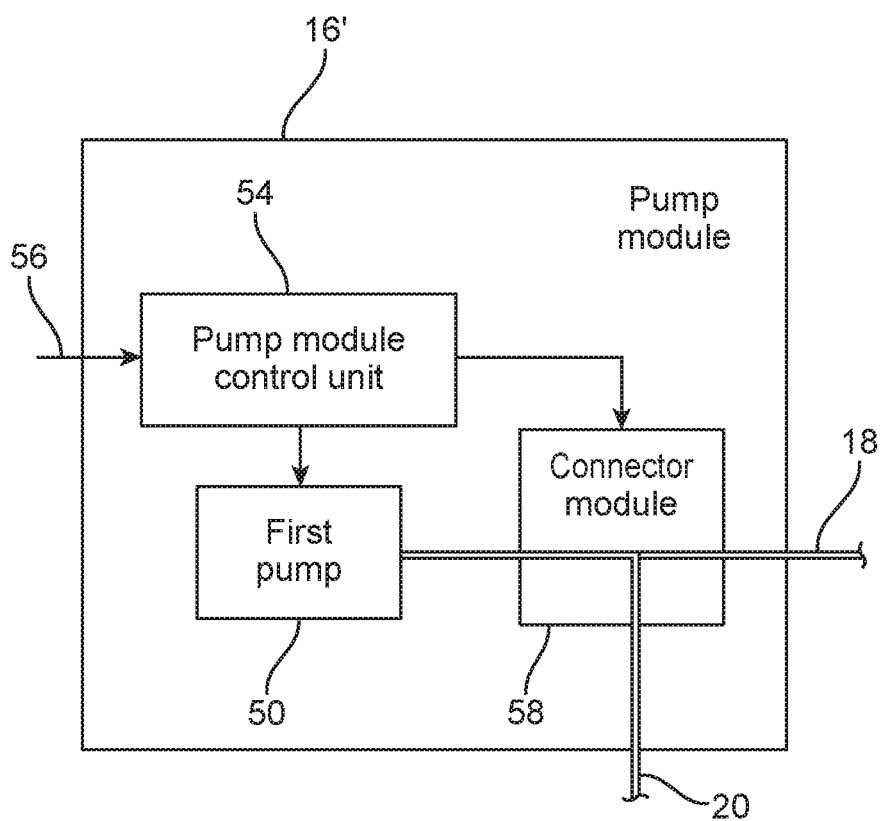

FIG. 6 schematically illustrates an exemplary pump module 16'. The pump module 16' comprises a first pump 50, a pump module control unit 54, and a connector module 58 such as a manifold. The first pump 50 is connected to an input of the connector module 58, and a first output of the connector module is connected to the first fluid port 24 (FIGS. 1-2) with the first fluid channel 18, a second output port of the connector module 58 is connected to the second fluid port 26 (FIGS. 1-2) with the second fluid channel 20. The connector module 58 is configurable to connect either the input port with the first output port, such that the first pump 50 is in fluid communication with the first fluid channel 18, or the input port with second output port, such that the first pump 50 is in fluid communication with the second fluid channel 20.

The pump module control unit 54 is connected to the processing unit 7 (FIGS. 1-2), wherefrom the pump module control unit 54 receives a pump module control signal 56. The pump module control unit 54 is connected to the first pump 50 and the connector module 58. The pump module control unit 54 controls the first pump 50 and the connector module 58 based on the pump module control signal 56. For example, in a first operating mode, e.g. when conducting the first audiologic test, the pump module 16' is configured to modify pressure in the first fluid channel 18, by utilizing the first pump 50 and configuring the connector module 58 to be in a first configuration, wherein the input of the connector module 58 is in fluid communication with the first output port of the connector module 58. Vice versa, in a second operating mode, e.g. when conducting the second audiologic test, the pump module 16' is configured to modify pressure in the second fluid channel 20, by utilizing the first pump 50 and configuring the connector module 58 to be in a second configuration, wherein the input port of the connector module 58 is in fluid communication with the second output port of the connector module 58. The pump module control unit 54 receives a pump module control signal 56 indicative of which of the fluid channels to modify pressure, the pump module control unit 54 control the first pump 50 and the connector module 58 based on the pump module control signal 56. The pump module 16' may further comprise one or more pressure sensors (not shown) for measuring the pressure in the first fluid channel 18 and/or in the second fluid channel 20.

Figure 7:
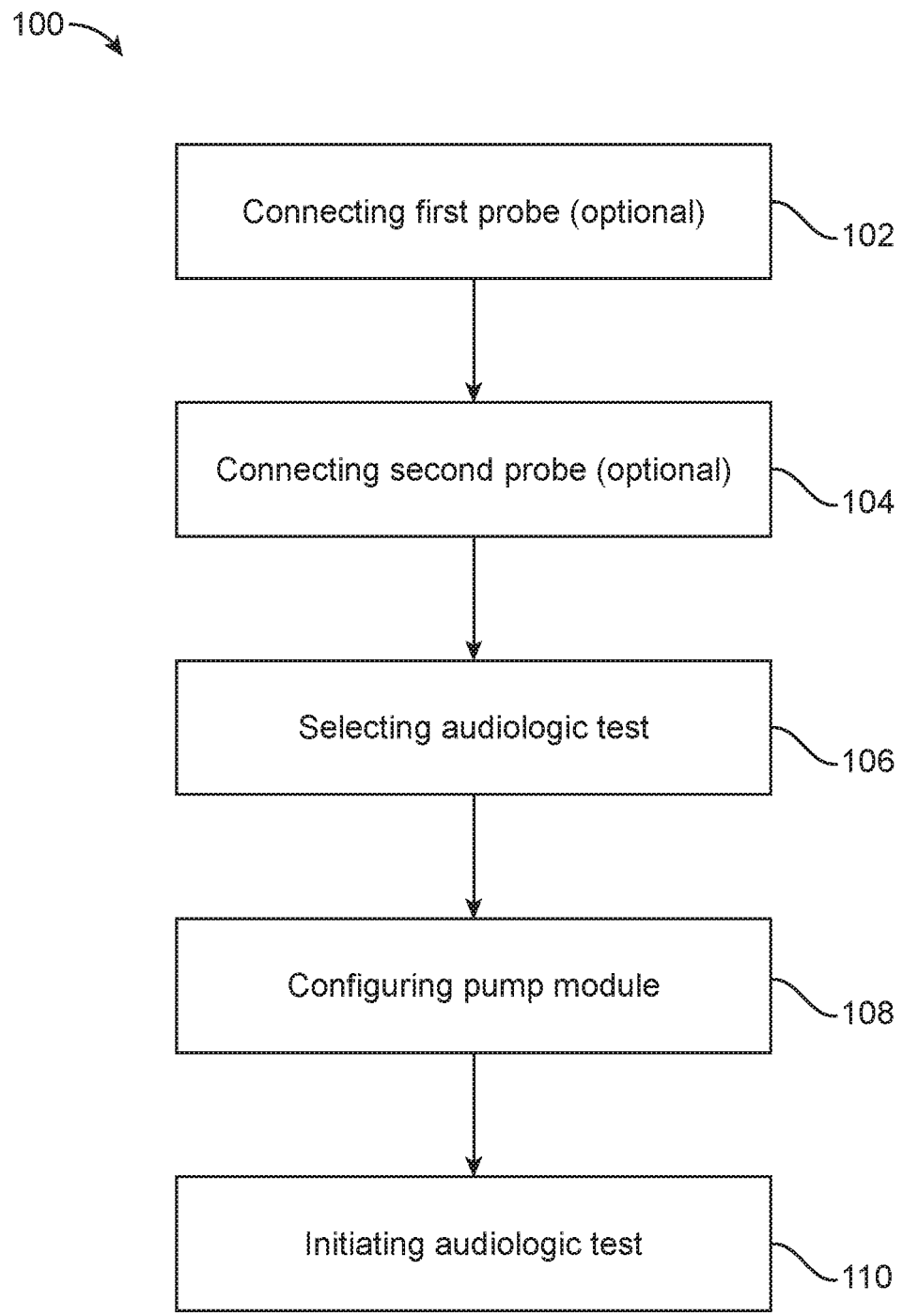
FIG. 7 shows a flow diagram of an exemplary method.

FIG. 7 shows a flow diagram of an exemplary method 100 for operating an audiologic test system, e.g. an audiologic test system 2, 2' as described in relation to any of the previous figures.

The method 100 comprises: connecting 102 a first probe 10 to a first probe connector 8, connecting 104 a second probe 14 to a second probe connector 12, selecting 106 an audiologic test, configuring 108 the pump module 16, 16', and optionally initiating 110 the audiologic test.

One or both steps of connecting 102 the first probe 10, and/or connecting 104 the second probe 14, may be omitted. For example, connecting 102 the first probe and/or connecting 104 the second probe are omitted if the audiologic test apparatus 4' and the first and/or second probes 10, 14 are not disconnectable, e.g. as illustrated in the example of FIG. 1. In another exemplary method (not illustrated), the steps of connecting 102 the first probe 10 and connecting 104 the second probe 14, are interchanged.

Selecting 106 an audiologic test may comprise selecting an audiologic test of a plurality of audiologic tests or a set of audiologic tests. For example, selecting 106 may comprise selecting an audiologic test of the first audiologic test and the second audiologic test. The first audiologic test may be a screening type acoustic reflex test. The second audiologic test may be a diagnostic type acoustic reflex test. In an embodiment, the audiologic test selection 106 may be performed automatically by the audiologic test system 2,2' e.g. based on detection of a probe selected from a probe holder.

Configuring 108 the pump module 16, 16' comprises configuring the pump module 16, 16' to be in fluid communication with the first fluid port 24 if the selected audiologic test is the first audiologic test, and configuring 108 the pump module 16, 16' comprises configuring the pump module 16, 16' to be in fluid communication with the second fluid port 26 if the selected audiologic test is the second audiologic test.

For example, selecting 106 an audiologic test is selected to be a diagnostic type acoustic reflex test, wherein the selection 106 was a selection between a screening type acoustic reflex test and a diagnostic type acoustic reflex test. The selection 106 may be performed in various ways, e.g. via a user interface, such as a touch screen, a designated button/selector switch, and/or using a method for detecting whether the first or second probe has been selected.

The method 100 comprises the step of initiating 110 the audiologic test selected, after configuring 108 the pump module 16, 16' according to the audiologic test selected.

Although particular embodiments have been shown and described, it will be understood that it is not intended to limit the claimed inventions. The specification and drawings are, accordingly, to be regarded in an illustrative rather than restrictive sense. The claimed inventions are intended to cover alternatives, modifications, and equivalents.

LIST OF REFERENCES 2, 2' audiologic test system
4, audiologic test apparatus
6 housing
7 processing unit
8 first probe connector
10 first probe
12 second probe connector
14 second probe
16, 16' pump module
18 first fluid channel
20 second fluid channel
22 user interface
23 control signal
24 first fluid port
26 second fluid port
28 tone generator
40 first microphone
42 first speaker
44 second microphone
46 second speaker
50 first pump
52 second pump
54 pump module control unit
56 pump module control signal
58 connector module
100 method
102 connecting first probe (optional)
104 connecting second probe (optional)
106 selecting audiologic test
108 configuring pump module
110 initiating audiologic test

The invention claimed is:

1. An audiologic test apparatus comprising:
a processing unit configured to conduct a set of audiologic tests including a first audiologic test and a second audiologic test;
a first probe connector for connecting a first probe for the first audiologic test, wherein the first probe connector is connected to the processing unit and comprises a first fluid port;
a second probe connector for connecting a second probe for the second audiologic test, wherein the second probe connector is connected to the processing unit and comprises a second fluid port; and
a pump module connected to the first fluid port with a first fluid channel and to the second fluid port with a second fluid channel, wherein the pump module in a first operating mode is configured to be in fluid communication with the first fluid port, and in a second operating mode is configured to be in fluid communication with the second fluid port, the pump module being configured to modify pressure in the first fluid channel when conducting the first audiologic test in the first operating mode, and to modify pressure in the second fluid channel when conducting the second audiologic test in the second operating mode.

2. The audiologic test apparatus according to claim 1, wherein the first audiologic test comprises a first set of subtests and the second audiologic test comprises the first set of subtests and a second set of subtests.

3. The audiologic test apparatus according to claim 1, wherein the first probe connector comprises one or more first terminals for electrically connecting the audiologic test apparatus and the first probe.

4. The audiologic test apparatus according to claim 1, wherein the processing unit is configured to select an audiologic test to be performed based on one or more control signals, wherein the selected audiologic test comprises the first audiologic test, the second audiologic test, or another audiologic test.

5. The audiologic test apparatus according to claim 4, further comprising a user interface, wherein the user interface comprises a selector with at least a first selector position and a second selector position, wherein the selector is connected to the processing unit, and wherein the one or more control signals comprises a selector signal indicative of at least the first selector position or the second selector position.

6. The audiologic test apparatus according to claim 4, wherein the one or more control signals comprise a first electrical probe signal from the first probe.

7. The audiologic test apparatus according to claim 1, wherein the pump module comprises a first pump and a second pump, wherein the first pump is connected to the first fluid port and the second pump is connected to the second fluid port.

8. The audiologic test apparatus according to claim 1, wherein the pump module comprises a first pump and a connector module, wherein the connector module is configured to connect the first pump and the first fluid port in the first operating mode, and the connector module is configured to connect the first pump and the second fluid port in the second operating mode.

9. The audiologic test apparatus according to claim 1, further comprising a first tone generator connected to the first probe connector, the first tone generator configured to generate a first primary test signal for the first probe when the first probe is connected to the first probe connector.

10. The audiologic test apparatus according to claim 9, wherein the first tone generator is configured to generate a first secondary test signal for the first probe when the first probe is connected to the first probe connector.

11. The audiologic test apparatus according to claim 1, wherein the processing unit is configured to detect a connection of the first probe to the first probe connector.

12. The audiologic test apparatus according to claim 1, wherein the processing unit is configured to configure the first audiologic test based on an identification signal indicative of the first probe.

13. The audiologic test apparatus according to claim 1, wherein the processing unit is configured to
initiate the first operating mode in response to the first probe being selected; and
initiate the second operating mode in response to the second probe being selected.

14. A method for operating an audiologic test system configured to conduct a set of audiologic tests including a first audiologic test and a second audiologic test, wherein the audiologic test system comprises a first probe configured for the first audiologic test, the first probe comprising a first fluid port, and wherein the audiologic test system further comprises a second probe configured for the second audiologic test, the second probe comprising a second fluid port, the audiologic test system comprising a pump module connected to the first fluid port and the second fluid port, the method comprising:
- connecting the first probe to a first probe connector of the audiologic test system;
- connecting the second probe to a second probe connector of the audiologic test system;
- selecting an audiologic test from the first audiologic test and the second audiologic test;
- configuring the pump module to be in fluid communication with the first fluid port if the selected audiologic test is the first audiologic test; and
- configuring the pump module to be in fluid communication with the second fluid port if the selected audiologic test is the second audiologic test.

15. An audiologic test system comprising:
- an audiologic test apparatus comprising a pump module and a processing unit configured to conduct a set of audiologic tests including a first audiologic test and a second audiologic test;
- a first probe configured for the first audiologic test, wherein the first probe is connected to the processing unit and comprises a first fluid port connected to the pump module; and
- a second probe configured for the second audiologic test, wherein the second probe is connected to the processing unit and comprises a second fluid port connected to the pump module;
- wherein the pump module is connected to the first fluid port with a first fluid channel and to the second fluid port with a second fluid channel, wherein the pump module in a first operating mode is configured to be in fluid communication with the first fluid port, and in a second operating mode is configured to be in fluid communication with the second fluid port, the pump module being configured to modify pressure in the first fluid channel when conducting the first audiologic test in the first operating mode, and to modify pressure in the second fluid channel when conducting the second audiologic test in the second operating mode.

16. The audiologic test system according to claim 15, wherein the first probe is configured to generate a first control signal indicative of the first audiologic test.

* * * * *